US012629269B2

(12) United States Patent
Kuroki et al.

(10) Patent No.: US 12,629,269 B2
(45) Date of Patent: May 19, 2026

(54) METHOD FOR MANUFACTURING STENT DELIVERY SYSTEM

(71) Applicant: TERUMO KABUSHIKI KAISHA, Tokyo (JP)

(72) Inventors: Takuya Kuroki, Fujinomiya (JP); Ryota Ikeuchi, Newton, MA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 19/077,298

(22) Filed: Mar. 12, 2025

(65) Prior Publication Data

US 2025/0288441 A1 Sep. 18, 2025

(30) Foreign Application Priority Data

Mar. 13, 2024 (JP) ................................. 2024-039213

(51) Int. Cl.
*A61F 2/958* (2013.01)
*A61F 2/95* (2013.01)

(52) U.S. Cl.
CPC ............ *A61F 2/9522* (2020.05); *A61F 2/958* (2013.01); *A61F 2/9524* (2020.05); *Y10T 29/49863* (2015.01)

(58) Field of Classification Search
CPC ... A61F 2/9524; A61F 2/958; Y10T 29/49863
See application file for complete search history.

(56) References Cited

U.S. PATENT DOCUMENTS

| | | | | |
|---|---|---|---|---|
| 7,886,419 B2 * | 2/2011 | Huang | .................... | A61F 2/958 29/283 |
| 8,261,423 B2 * | 9/2012 | Jow | ......................... | B29C 65/72 29/515 |
| 8,333,000 B2 * | 12/2012 | Huang | .................... | A61F 2/958 623/1.11 |
| 8,752,265 B2 * | 6/2014 | Wang | ..................... | B29D 23/00 29/515 |
| 9,295,570 B2 * | 3/2016 | Schwager | ................. | A61F 2/91 |
| 2003/0055482 A1 * | 3/2003 | Schwager | ............... | A61F 2/958 623/1.11 |
| 2013/0025110 A1 * | 1/2013 | Stankus | .................. | A61F 2/915 29/505 |
| 2014/0096357 A1 * | 4/2014 | Wang | ...................... | A61F 2/958 29/446 |
| 2014/0230227 A1 * | 8/2014 | Wang | ..................... | A61F 2/958 29/516 |
| 2019/0375146 A1 * | 12/2019 | Wang | .................... | A61F 2/9522 |

FOREIGN PATENT DOCUMENTS

JP 2012070912 A 4/2012

* cited by examiner

*Primary Examiner* — Jermie E Cozart
(74) *Attorney, Agent, or Firm* — Buchanan Ingersoll & Rooney PC

(57) ABSTRACT

A method for manufacturing a stent delivery system that includes a first diameter reduction step including a first compression step of compressing a stent inward in a radial direction of the stent in a state where a balloon is inserted into a tube of the stent formed in a tubular shape to reduce diameters of the stent and the balloon, and a first release step of releasing the compression thereafter. A pressurization step of supplying fluid to the balloon to inflate the balloon and pressing the balloon against the inner side of the stent is performed during the first release step or after the first release step.

18 Claims, 8 Drawing Sheets

METHOD FOR MANUFACTURING STENT DELIVERY SYSTEM

CROSS-REFERENCES TO RELATED APPLICATIONS

This application claims priority to Japanese Application No. 2024-039213 filed on Mar. 13, 2024, the entire content of which is incorporated herein by reference.

TECHNOLOGICAL FIELD

The present disclosure relates to a method for manufacturing a stent delivery system.

BACKGROUND DISCUSSION

Japanese Patent Application Publication No. 2012-070912 A discloses a method for manufacturing a stent delivery system in which a stent is crimped on a balloon catheter. In the method for manufacturing a stent delivery system, the prepared stent is deflated in advance to a second diameter having an inner diameter equal to or smaller than an outer diameter of a folded balloon, the folded balloon is inserted into the stent, and pressure is further applied radially inward from an outer surface of the stent to deflate the stent to a third diameter which is a diameter at which crimping is completed. It is considered that it is possible to manufacture a stent delivery system capable of preventing the stent from falling off or moving in this method for manufacturing a stent delivery system.

In the stent delivery system, if a holding force of the stent in a state of being crimped on the balloon of the balloon catheter, that is, retention greatly varies, the stent with small retention falls off from the balloon in some cases. However, there is a case where the variation in the retention cannot be sufficiently reduced, for example, in the related art disclosed in Japanese Patent Application Publication No. 2012-070912 A. Therefore, in the balloon catheter, it is desired to reduce the variation in the holding force of holding the stent on the balloon, that is, to stabilize the retention.

SUMMARY

A method is disclosed for manufacturing a stent delivery system which achieves stabilization of retention of a balloon catheter on which a stent is crimped.

A method for manufacturing a stent delivery system according to the present disclosure for achieving the above object is as follows.

[1] A method for manufacturing a stent delivery system, the method including: a first diameter reduction step including a first compression step of compressing a stent inward in a radial direction of the stent in a state where a balloon is inserted into a tube of the stent formed in a tubular shape to reduce diameters of the stent and the balloon, and a first release step of releasing the compression after the first compression step; and a pressurization step of supplying fluid to the balloon to inflate the balloon and pressing the balloon against the inner side of the stent, wherein the pressurization step is performed during or after the first release step.

[2] The method for manufacturing a stent delivery system according to [1], further including a second diameter reduction step performed after the first diameter reduction step, the second diameter reduction step including a second compression step of compressing the stent inward in the radial direction of the stent to reduce the diameters of the stent and the balloon, and a second release step of releasing the compression after the second compression step, wherein the pressurization step is performed during the second compression step.

[3] The method for manufacturing a stent delivery system according to [2], wherein the pressurization step is performed during a period from the first release step to the second compression step immediately after the first release step.

[4] The method for manufacturing a stent delivery system according to [2], wherein the pressurization step is performed over a period from before the first release step to after the second compression step immediately after the first release step.

[5] The method for manufacturing a stent delivery system according to [2], wherein the pressurization step is performed after the first release step and before the second compression step immediately after the first release step.

[6] The method for manufacturing a stent delivery system according to any one of [3] to [5], wherein the pressurization step includes a holding step of keeping pressure of the fluid supplied to the balloon and the diameter of the stent constant for a predetermined period of time.

[7] The method for manufacturing a stent delivery system according to any one of [2] to [6], wherein the second diameter reduction step is repeated twice (two times) or more.

[8] The method for manufacturing a stent delivery system according to any one of [1] to [7], wherein the pressurization step in the first release step makes the diameter of the stent larger than a recoil diameter at which the stent is recoiled by the first release step.

[9] A method for manufacturing a stent delivery system, the method comprising: compressing a stent inward a first time in a radial direction of the stent in a state where a balloon is inserted into a tube of the stent formed in a tubular shape to reduce diameters of the stent and the balloon, and releasing the compression after the compressing of the stent inward the first time; and supplying fluid to the balloon to inflate the balloon and pressing the balloon against an inner side of the stent.

[10] A method for manufacturing a stent delivery system, the method comprising: compressing a stent inward at a load of 5 N to 10 N per length of 1 mm in an axial direction of the stent inward in a radial direction of the stent in a state where a balloon is inserted into a tube of the stent formed in a tubular shape to reduce diameters of the stent and the balloon; releasing the compression after the compressing of the stent; and supplying fluid to the balloon to inflate the balloon and pressing the balloon against an inner side of the stent.

According to the present disclosure, it is possible to provide the method for manufacturing a stent delivery system which achieves the stabilization of the retention of the balloon catheter on which the stent is crimped.

DETAILED DESCRIPTION

A method for manufacturing a stent delivery system according to an embodiment of the present disclosure will be described with reference to the drawings.

Figure 1:
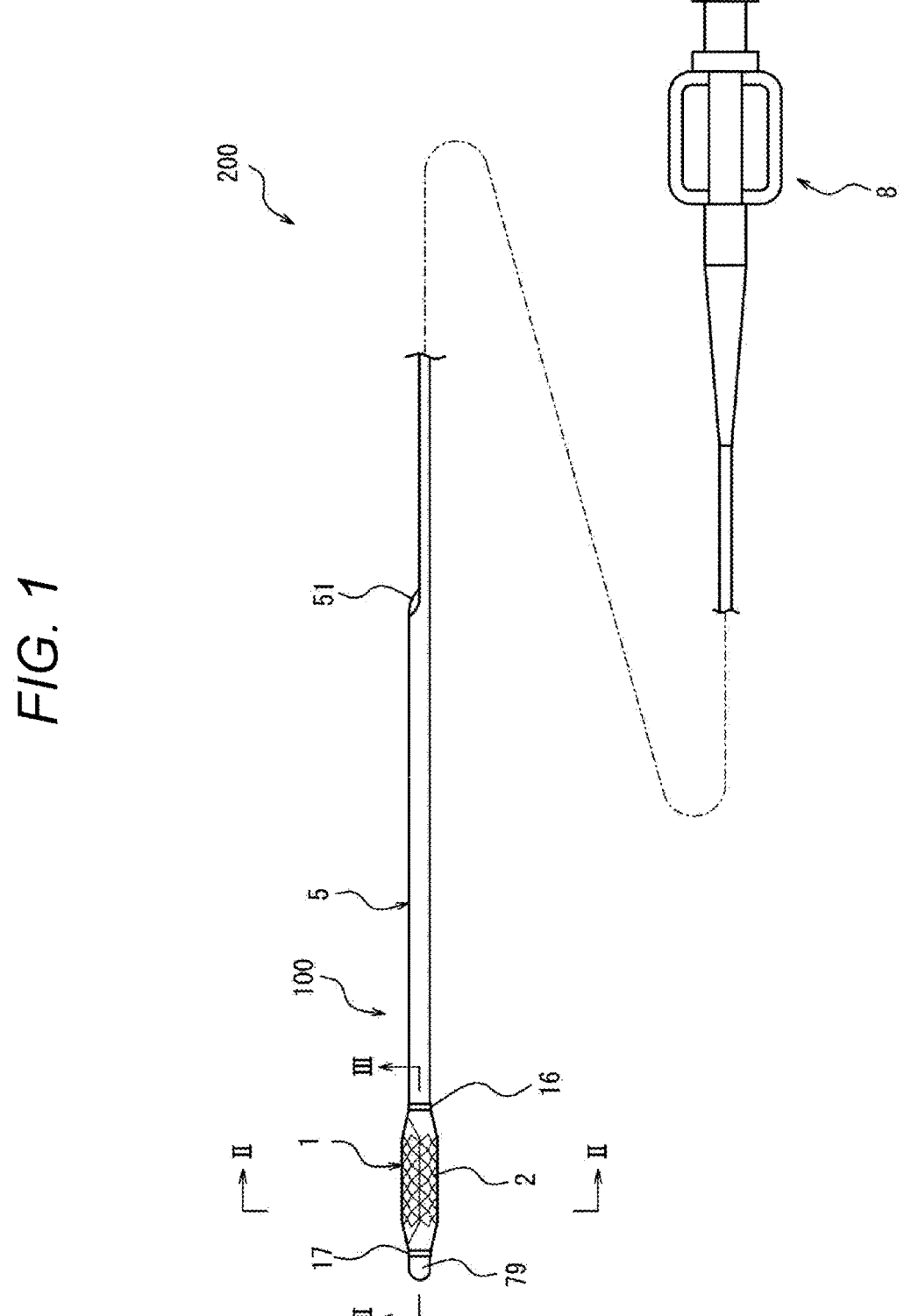
FIG. 1 is an explanatory view of a stent delivery system.

FIG. 1 illustrates a stent delivery system 200 achieved by the method for manufacturing a stent delivery system according to the present embodiment.

Figure 2:
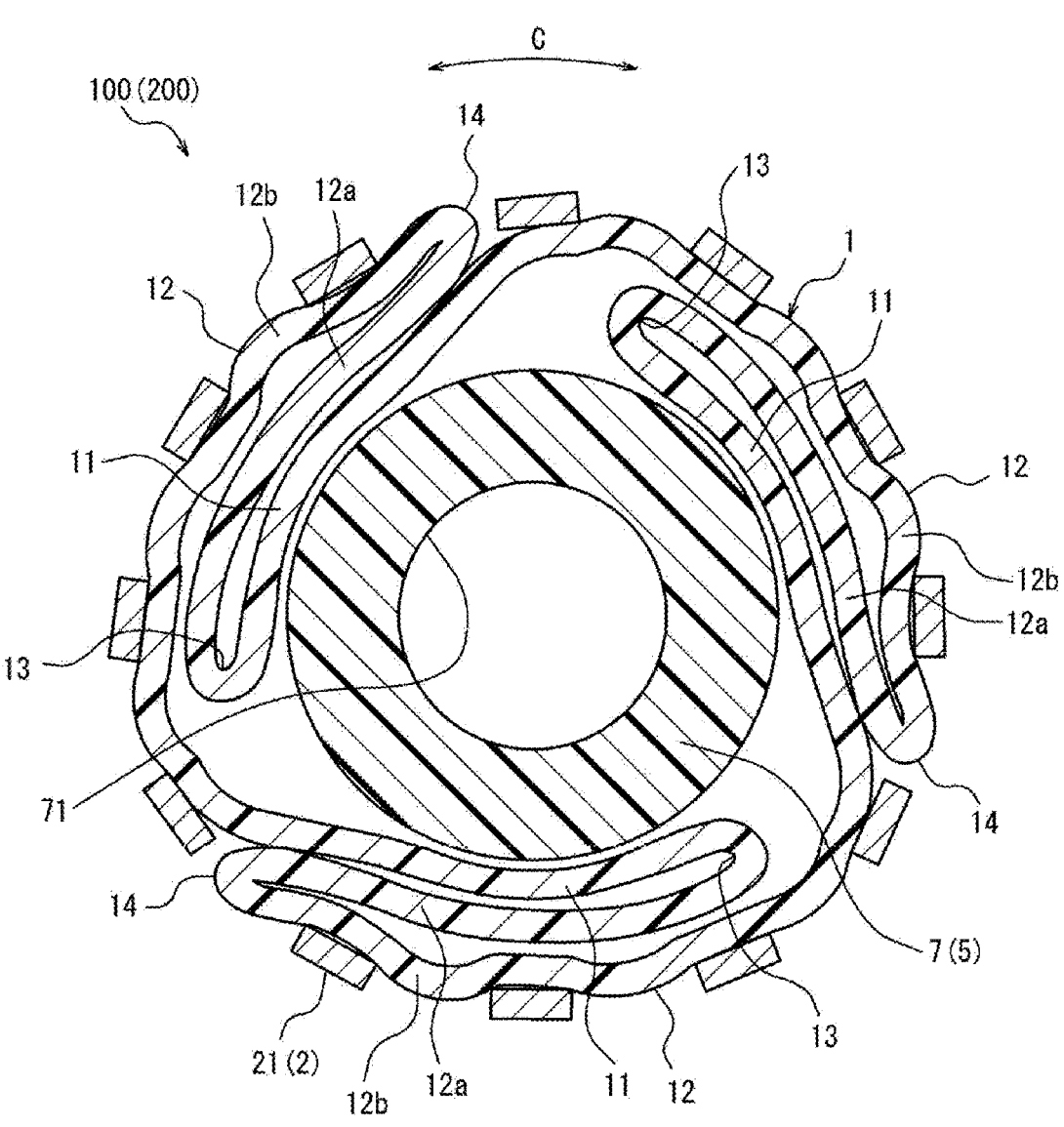
FIG. 2 is a cross-sectional view taken along line II-II in FIG. 1.

FIG. 2 is a cross-sectional view taken along line II-II in FIG. 1. First, an outline of the stent delivery system 200 and the method for manufacturing the same will be described.

As illustrated in FIG. 1, the stent delivery system 200 includes a balloon catheter 100 having a balloon 1 inflated or deflated by supply or discharge of fluid, and a stent 2 disposed on the balloon 1 and formed in a tubular shape.

As illustrated in FIG. 2, the stent 2 allows the balloon 1 inserted into a tube (i.e., tubular portion) of the stent 2, and is fixed on an outer peripheral surface of the balloon 1. That is, the stent 2 is crimped on the balloon 1. Note that the balloon 1 is in a deflated state in FIGS. 1 and 2.

The stent delivery system 200 can be manufactured by the method for manufacturing a stent delivery system, the method including a diameter reduction step of compressing the stent 2 inward in a radial direction of the stent 2 to reduce diameters of the stent 2 and the balloon 1 and then releasing the compression in a state where the balloon 1 is inserted into the tube of the stent 2 formed in the tubular shape.

Hereinafter, the stent delivery system and the method for manufacturing the same will be described in detail.

The stent delivery system 200 including the balloon catheter 100 illustrated in FIG. 1 is a medical device used for a procedure (for example, PCI (percutaneous coronary intervention)) of pushing and widening a lesion (stenosed site) formed in a living body lumen such as a blood vessel. In the procedure using the stent delivery system 200, an operator inserts the stent 2 crimped on the balloon 1 disposed at a distal portion of a shaft 5 into the living body lumen. The operator expands the balloon 1 on the inner peripheral side of the stenosed site formed in the living body lumen, and expands the stent 2 together with the balloon 1. The operator can maintain the stenosed site being pushed and widened by placing the expanded stent 2 on the inner peripheral side of the stenosed site.

Note that the balloon catheter 100 is used to deliver the stent 2 to the stenosed site, but can also be configured to be used for the purpose of, for example, treating and improving a stenosed site formed in a living body organ such as a blood vessel, a bile duct, a trachea, an esophagus, other digestive tract, a urethra, a lumen in the ears and nose, or other organs.

Figure 3:
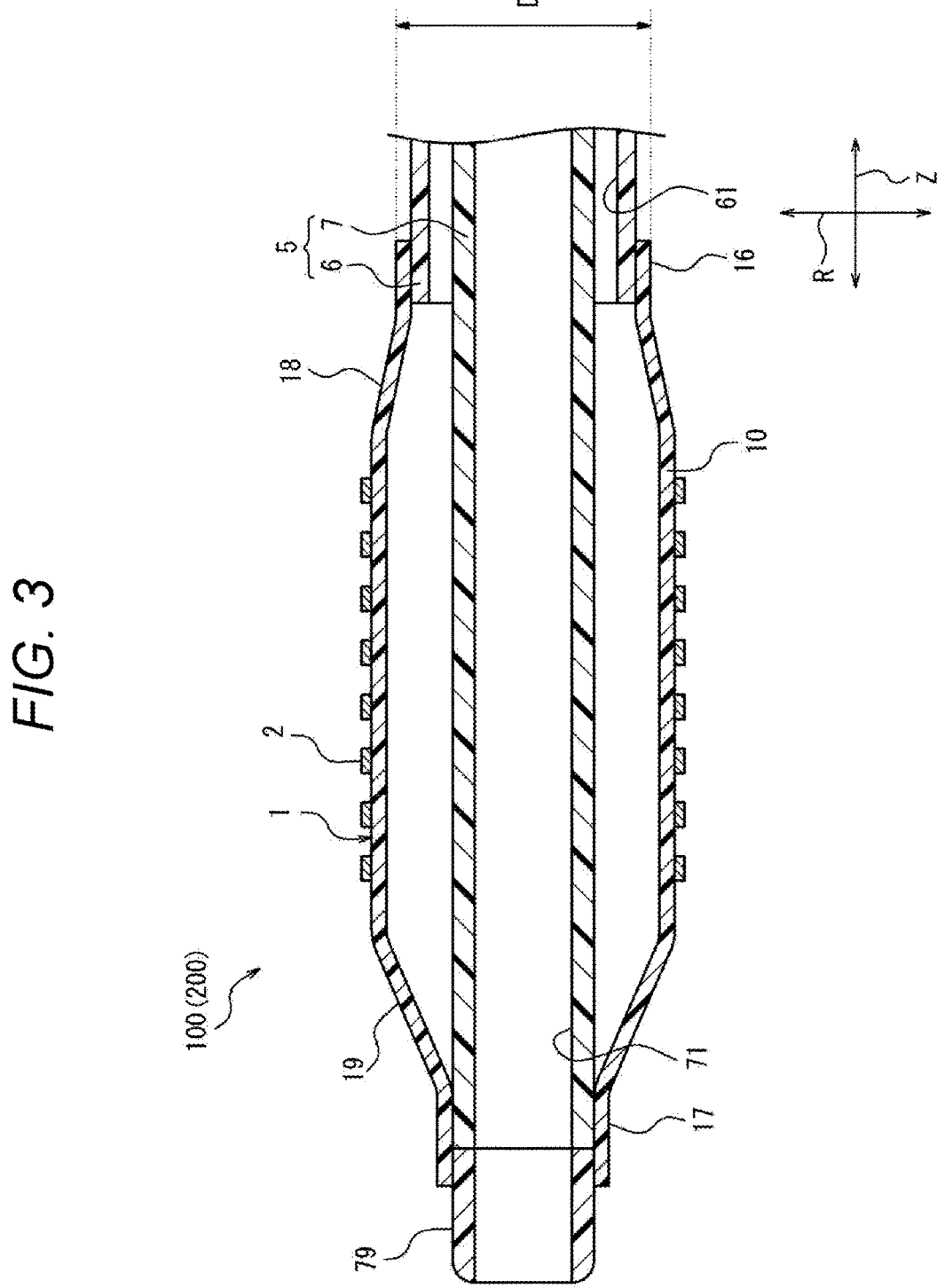
FIG. 3 is a cross-sectional view of a balloon, a stent, a portion of a shaft supporting the balloon, and the periphery of these members.

As illustrated in FIGS. 1 to 3, the balloon catheter 100 includes the shaft 5 having flexibility and an elongated shape, the balloon 1 disposed at the distal portion of the shaft

5, and a hub 8 (see FIG. 1) disposed at a proximal portion of the shaft 5. In the stent delivery system 200 (see FIG. 1), the stent 2 is crimped on the balloon 1 of the balloon catheter 100. Note that FIG. 3 is a cross-sectional view at a position corresponding to arrow III-III in FIG. 1, and is a cross-sectional view of the balloon 1 in an expanded state, the stent 2, and a portion of the shaft 5 supporting the balloon 1 and the periphery of these members. FIG. 3 illustrates a cross section overlapping an axial center of the shaft 5.

The balloon catheter 100 may be provided with a guide wire port 51 through which a guide wire or the like is led out closer to the distal portion side of the shaft 5.

As illustrated in FIG. 3, the shaft 5 includes an inner tube 7 in which a lumen 71 through which the guide wire or the like is inserted is formed, and an outer tube 6 forming a lumen 61 through which a pressurizing medium (for example, fluid such as saline or contrast) can flow between the inner tube 7 and the outer tube 6. The shaft 5 has a double tube structure in which the inner tube 7 and the outer tube 6 are concentrically disposed by inserting the inner tube 7 into the outer tube 6.

The shaft 5 supports the balloon 1. The inner tube 7 of the shaft 5 passes through the balloon 1. The shaft 5 supplies the above-described fluid to a space in the balloon 1 or discharges the fluid from the balloon 1, thereby inflating or deflating the balloon 1.

The balloon 1 is liquid-tightly and airtightly joined to a distal portion of the inner tube 7 by welding or the like. A distal portion of the balloon 1 in an extending direction of the shaft 5 is joined to the inner tube 7 by fusion or the like. In addition, a proximal portion of the balloon 1 in an extending direction of the shaft 5 is joined to the outer tube 6 by fusion or the like. In FIG. 3, a portion of the balloon 1 where the distal portion of the balloon 1 and the inner tube 7 are joined is illustrated as a distal-side joint portion 17. In addition, a portion of the balloon 1 where the proximal portion of the balloon 1 and the outer tube 6 are joined is illustrated as a proximal-side joint portion 16. A diameter D of the proximal-side joint portion 16 is larger than a diameter (outer diameter) of the distal-side joint portion 17.

A distal tip 79 may be attached to a distal end of the inner tube 7 to protect a biological organ (for example, an inner wall of a blood vessel) from damage when, for example, a distal end of the balloon catheter 100 comes into contact with the biological organ. The distal tip 79 can be configured using, for example, a resin material more flexible than that of the inner tube 7.

The pressurizing medium can flow into a space (hereinafter, referred to as an internal space) between the balloon 1 and the inner tube 7.

The balloon 1 is inserted into the living body lumen and is folded to keep the performance in passing through the inside of the living body lumen until reaching the stenosed site in the living body lumen.

The balloon 1 expands when the pressurizing medium flows into the internal space (see FIG. 3). When the balloon 1 expands, the balloon catheter 100 is expanded in diameter such that a part of the balloon 1 presses the stent 2 against the stenosed site formed in the living body lumen. The stent 2 is placed in a state of being expanded in diameter by the balloon 1 while pushing and widening the stenosed site.

The balloon 1 is inserted into the living body lumen and is folded in a deflated state in order to keep the performance in passing through the inside of the living body lumen until reaching the stenosed site in the living body lumen (see FIG.

2). Note that the deflated state of the balloon 1 is a state where the pressurizing medium does not flow into the internal space.

As illustrated in FIG. 2, the balloon 1 may be divided into three or more regions and folded along a circumferential direction (direction C in FIG. 2) of the inner tube 7. In FIG. 2, each of the regions of the balloon 1 is folded so as to have a wing base 11 adjacent to the inner tube 7 and along the inner tube 7, and a wing 12 stacked on the wing base 11.

The wing 12 in each of the regions is stacked on the wing base 11 along the same direction in the circumferential direction. The wing 12 has an inner portion 12a is stacked adjacently on the wing base 11 and an outer portion 12b stacked on the inner portion 12a.

A boundary portion between the wing base 11 and the wing 12, that is, the boundary portion between the wing base 11 and the wing 12 placed on the wing base 11 is a fold portion 13 along an axial direction (direction Z in FIG. 3) of the inner tube 7. The fold portion 13 is located on the inner side of the outer portion 12b in a radial direction (direction R in FIG. 3) of the inner tube 7.

An end portion of the inner portion 12a, which is a boundary portion between the inner portion 12a and the outer portion 12b and on the opposite side of the fold portion 13 in the circumferential direction of the inner tube 7, is a fold portion 14 along the axial direction of the inner tube 7.

As illustrated in FIG. 3, as for a size of the balloon 1 in the time of expansion, for example, a straight portion 10 has an outer diameter of about 1 mm to 20 mm and preferably about 1 mm to 10 mm, and a length in the axial direction (direction Z) of about 5 mm to 100 mm and preferably about 5 mm to 60 mm. In addition, the distal-side joint portion 17 has an outer diameter of about 0.3 mm to 1.5 mm and preferably about 0.5 mm to 1.3 mm, and a length in the axial direction of about 0.5 mm to 5 mm and preferably about 0.5 mm to 3 mm. The proximal-side joint portion 16 has an outer diameter of about 0.5 mm to 1.8 mm and preferably about 0.6 mm to 1.3 mm, and a length in the axial direction of about 1 mm to 8 mm and preferably about 1 mm to 6 mm. Furthermore, lengths of a distal tapered portion 19 and a proximal tapered portion 18 are about 1 mm to 10 mm and preferably about 3 mm to 7 mm.

As a material for forming the balloon 1, for example, an organic polymer material can be used. As the organic polymer material forming the balloon 1, specifically, a polymer material such as polyolefins (for example, polyethylene, polypropylene, polybutene, an ethylene-propylene copolymer, an ethylene-vinyl acetate copolymer, an ionomer, or a mixture of two or more kinds of polyolefins), polyvinyl chloride, polyamide, polyamide elastomer, polyurethane, polyurethane elastomer, polyimide, or fluororesin, or a mixture of the polymer materials described above, or an elastic resin material such as the two or more polymer materials described above can be used, and among them, a polyamide-based resin can be suitably used as a main material.

The stent 2 is a member formed in the tubular shape as illustrated in FIG. 3. The stent 2 is made of a metal alloy as an example. The stent 2 is a wire mesh member formed in a tubular shape as an example. The balloon 1 is inserted into the tube of the stent 2. The stent 2 is fixed (crimped) on an outer surface of the balloon 1. In a state where the stent 2 is fixed on the outer surface of the balloon 1, the radial direction of the stent 2 is the same as the radial direction of the inner tube 7. Hereinafter, the radial direction of the stent 2 and the radial direction of the inner tube 7 is sometimes collectively referred to simply as the radial direction.

Figure 4:
FIG. 4 is an exploded view of the stent.

FIG. 4 illustrates an exploded view of the stent 2. As illustrated in FIG. 4, the stent 2 includes a plurality of annular portions 21 extending in a wave shape in the circumferential direction of the inner tube 7 (see FIG. 2) and disposed at predetermined intervals in the axial direction of the inner tube 7, and a plurality of link portions 22 each connecting the adjacent annular portions 21 to one another in the axial direction. The stent 2 is configured in the tubular shape. The balloon 1 is inserted inside the tube of the stent 2 (see FIGS. 2 and 3).

The stent 2 is designed to maintain the state of being fixed (crimped) on the outer surface of the balloon 1 and to maintain its expanded diameter once expanded by the balloon 1. Therefore, as the material of the stent 2, a material that is plastically deformed by expansion of the balloon 1 and maintains a shape after the expansion of the balloon 1 can be selected.

The metal alloy forming the stent 2 may contain at least one or more selected from cobalt, chromium, nickel, tungsten, molybdenum, iron, and platinum as an alloy component. Particularly suitable as the metal alloy forming the stent 2 can include, for example, L-605 alloy which is an alloy containing cobalt, chromium, tungsten and nickel.

The expanded diameter of the stent 2 is not particularly limited, and can be, for example, 1 mm to 30 mm in outer diameter. The stent 2 according to the present embodiment is used to treat a lesion such as a stenosed site or an occluded site generated in a blood vessel, a bile duct, a trachea, an esophagus, a urethra, or other living body lumens. The expanded diameter of the stent 2 is set according to a diameter of the target lesion.

A diameter of the stent 2 in a state of being attached to the balloon catheter 100 before expansion is not particularly limited, and can be, for example, 0.5 mm to 3 mm in outer diameter. When a diameter of a lumen in which the target lesion is present is small, the diameter in the state of being attached to the balloon catheter 100 also needs to be small.

A diameter of the stent 2 in a state before expansion and before being attached to the balloon catheter 100 is not particularly limited, and can be, for example, 1 mm to 5 mm in outer diameter. The stent 2 is manufactured using a known technique, and can be manufactured, for example, by removing an unnecessary portion other than a region to form a strut from a pipe material and then polishing the resultant. Thereafter, the stent 2 is reduced in diameter and attached to the balloon catheter 100. In this case, the outer diameter in the state before being attached to the balloon catheter 100 is an outer diameter of the stent 2 after being polished and is substantially the same as an outer diameter of the pipe material.

A thickness of the stent 2 is not particularly limited, and can be, for example, 0.05 mm to 1 mm.

A line width of the stent 2 is not particularly limited, and can be, for example, 0.05 mm to 1 mm.

An angle formed by a bent portion (hereinafter, referred to as a bent portion) in the annular portion 21 of the stent 2 is not particularly limited, and can be, for example, 10° to 120° at the time of uniform expansion.

An axial length of the link portion 22 is not particularly limited, and can be, for example, 0.05 mm to 50 mm. The link portion 22 may have a circumferentially extending component, but a circumferential length at that time is not particularly limited, and can be, for example, 0.05 mm to 50 mm.

A surface of the stent 2 may be coated with a drug such as an immunosuppressive agent. As a result, restenosis in the living body lumen after stent placement is prevented. Since the bent portion has a risk that stress concentration occurs at the time of expansion and the drug is peeled off, the bent portion is not necessarily coated with the drug.

In addition, for example, as in a stent graft, a cover member made of a fibrous material, a sheet-like material, or the like may be disposed on an outer surface or an inner surface of the stent 2. The permeability of the cover member to liquid or gas may be high or low. In addition, the cover member may be impermeable.

The stent 2 is crimped on the balloon 1 as follows. Hereinafter, as a method for manufacturing the stent delivery system 200, a method (hereinafter, referred to as a crimping method) of crimping the stent 2 by crimping the stent 2 to the balloon 1 will be described.

The crimping method according to the present embodiment includes: a first diameter reduction step of compressing the stent 2 inward in the radial direction of the stent 2 to reduce diameters of the stent 2 and the balloon 1 in a state where the balloon 1 is inserted into the tube of the stent 2 and then releasing the compression; and a pressurization step of supplying fluid to the balloon 2 to inflate the balloon 2 and pressing the balloon 1 against the inner side of the stent 2. In addition, the crimping method according to the present embodiment may include a second diameter reduction step performed after the first diameter reduction step to compress the stent 2 inward in the radial direction of the stent 2 to reduce the diameters of the stent 2 and the balloon 1, and then release the compression. The first diameter reduction step and the second diameter reduction step are operations of crimping the stent 2 to the balloon 1.

The first diameter reduction step is the operation including compression of the stent 2 and release of the compression. In the first diameter reduction step, the balloon 1 is provided with folds of the fold portions 13 and 14 (see FIG. 2) (the balloon 1 has a fold-up shape). The second diameter reduction step is an operation including compression and release of the compression performed after the first diameter reduction step. The first diameter reduction step and the second diameter reduction step may be repeated twice (two times) or more. The operation of reducing the diameters of the stent 2 and the balloon 1 in the first diameter reduction step and the operation of reducing the diameters of the stent 2 and the balloon 1 in the second diameter reduction step are the same operation in the basic part and are partially different.

The first diameter reduction step includes a first compression step of compressing the stent 2 inward in the radial direction of the stent 2 to reduce the diameter of the stent 2 to a first diameter, and a first release step of releasing the compression after the first compression step.

The first diameter reduction step may include a first maintenance step of maintaining the stent 2 at a first diameter. That is, the first diameter reduction step may include the first compression step of compressing the stent 2 inward in the radial direction of the stent 2 to reduce the diameter of the stent 2 to the first diameter, the first maintenance step of maintaining the stent 2 at the first diameter, and the first release step of releasing the compression after the first maintenance step. The first compression step, the first maintenance step, and the first release step are performed in this order.

In the first release step, the diameter of the stent 2 is enlarged by releasing the compression (so-called recoil). Note that the recoil means that the stent 2 naturally expands in diameter by an amount of deformation due to elastic deformation at the time of diameter reduction of the stent 2. In the first release step, the diameter of the stent 2 is made larger by the pressurization step to be described later than a recoil diameter at which the stent 2 is completely recoiled in the first release step. The pressurization step will be described later. The first release step may be repeated twice (two times) or more by repeating the second diameter reduction step. In the present embodiment, "the stent 2 is completely recoiled" means that the stent 2 is expanded in diameter to the maximum diameter by the recoil, and the recoil diameter means the maximum diameter of the stent 2 expanded in diameter by the recoil.

In addition, the second diameter reduction step includes a second compression step of compressing the stent 2 inward in the radial direction of the stent 2 to reduce the diameter of the stent 2 to a second diameter, and a second release step of releasing the compression after the second compression step. When the second diameter reduction step is performed in addition to the first diameter reduction step, it is possible to further decrease the diameter of the stent 2 as the folds of the respective fold portions 13 and 14 (see FIG. 2) of the balloon 1 become settled or the space in the balloon 1 decreases, as compared with a case where only the first diameter reduction step is performed. As a result, cross-sectional shapes of the balloon 1 and the stent 1 are made relatively uniform, a variation in a holding force (retention) of holding the stent 2 on the balloon 1 is reduced, and the retention is stabilized. In addition, through the second diameter reduction step, an amount of the balloon 1 pinched by the stent 2 increases or the like, so that the stent 2 is more stably fixed to the balloon 1. As a result, the variation in the holding force (retention) of holding the stent 2 on the balloon 1 in the balloon catheter 100 is reduced, and the retention is stabilized.

Hereinafter, reducing the variation in the holding force of holding the stent 2 on the balloon 1 in the balloon catheter 100 is sometimes simply referred to as stabilizing the retention or stabilization of the retention.

The second diameter reduction step is preferably repeated twice (two times) or more. As a result, the diameter is further decreased, and the retention is stabilized. When the second diameter reduction step is performed three times or more and twenty times or less, a sufficient decrease in the diameter and sufficient stabilization in the retention can be achieved.

The second diameter reduction step may include a second maintenance step of maintaining the stent 2 at the second diameter. That is, the second diameter reduction step may include the second compression step of compressing the stent 2 inward in the radial direction of the stent 2 to reduce the diameter of the stent 2 to the second diameter, the second maintenance step of maintaining the stent 2 at the second diameter, and the second release step of releasing the compression after the second maintenance step. The second compression step, the second maintenance step, and the second release step are performed in this order.

Figure 5:
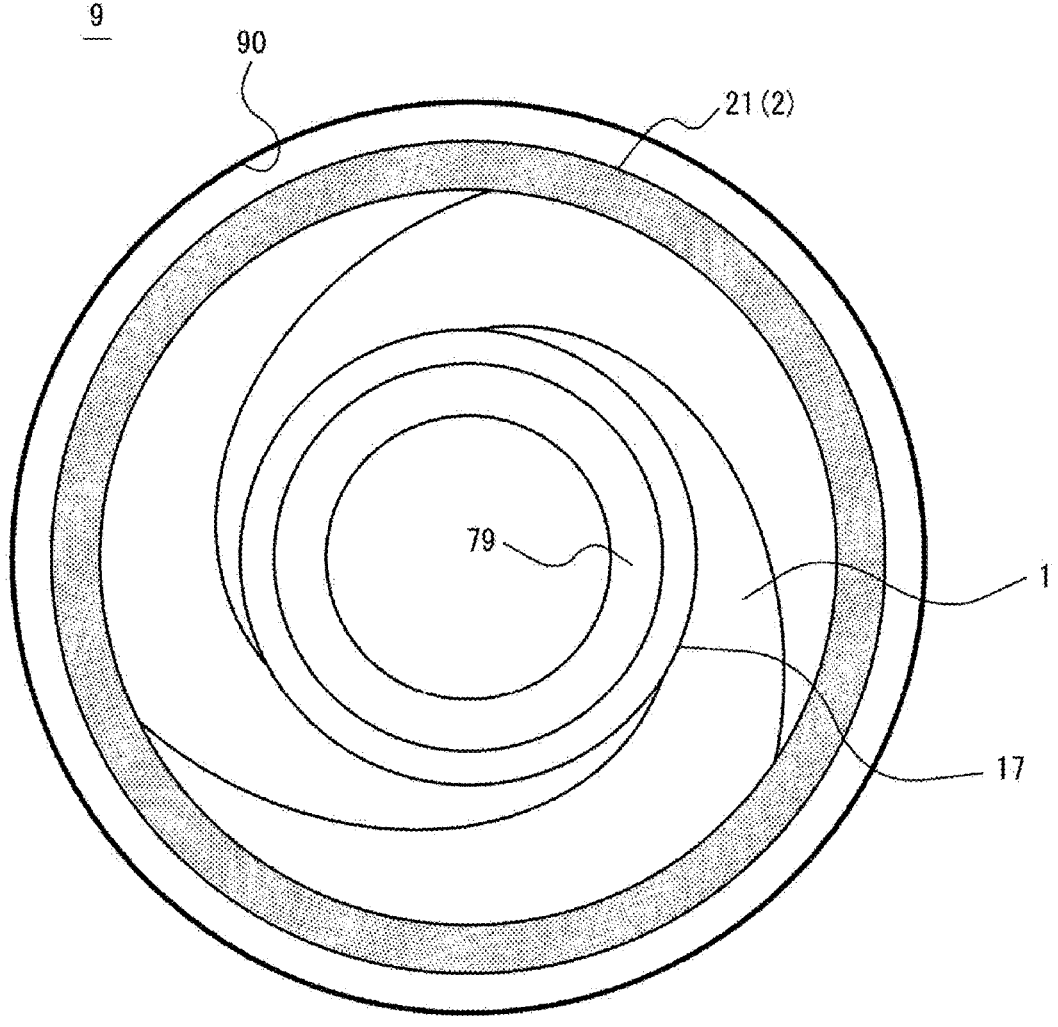
FIG. 5 is an explanatory view of states of the balloon, the stent, and a crimping head before a diameter of the stent is reduced in a crimping operation.
Figure 6:
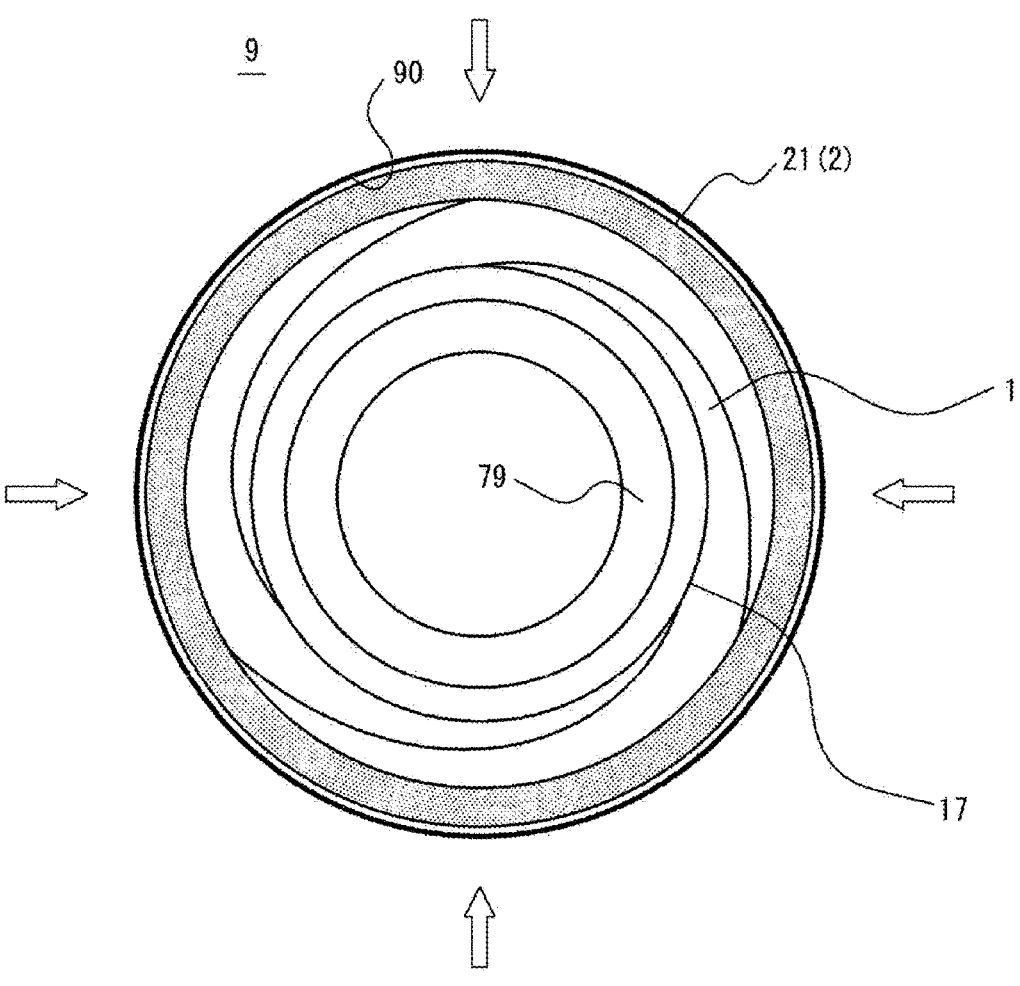
FIG. 6 is an explanatory view of states of the balloon, the stent, and the crimping head after the diameter of the stent is reduced in the crimping operation.

The diameter reduction of the stent 2 in the first diameter reduction step (first compression step) and the second diameter reduction step (first compression step) may be a crimping operation by a crimping head 9 of a crimping device as illustrated in FIGS. 5 and 6. Note that FIGS. 5 and 6 are explanatory views of images of states of the balloon 1, the stent 2, and the crimping head 9 before the diameter of the stent 2 is reduced and after the diameter of the stent 2 is reduced in this order in the crimping operation.

The crimping head 9 has a hole portion 90 having a straight body shape whose inner diameter can be reduced and enlarged. The diameter reduction of the stent 2 can be performed by inserting the balloon 1 to which the stent 2 is fixed into the hole portion 90, reducing a diameter (hereinafter, sometimes referred to as an opening diameter of the crimping head 9) of the hole portion 90, and pressing, that is, compressing an outer peripheral surface of the stent 2 along the radial direction. The compression of the stent 2 can be released by enlarging the opening diameter of the crimping head 9.

The diameter reduction of the stent 2 in each of the first diameter reduction step and the second diameter reduction step is preferably performed by applying a load of 5 N (newtons) or more and 10 N or less (5 N to 10 N) per length of 1 mm in the axial direction (direction Z in FIG. 3) of the stent 2 inward in the radial direction. As a result, the stent 2 can be crimped on the balloon 1 without damaging the balloon 1, and the diameters (outer diameters) of the stent 2 and the balloon 1 can be decreased. Hereinafter, decreasing the diameter of the stent 2 is sometimes simply referred to as a decrease in diameter or decreasing the diameter. The concept of the decrease in diameter or decreasing the diameter includes the case of decreasing the diameters of the stent 2 and the balloon 1. In the following description, when simply described as the diameter of the stent 2, it means the outer diameter of the stent 2.

In the first diameter reduction step, the opening diameter of the crimping head 9 may be reduced to the first diameter. As a result, the diameter reduction of the stent 2 can be performed until the diameter of the stent 2 reaches the first diameter.

The first maintenance step is a step of stopping, after the diameter of the stent 2 reaches the first diameter in the first compression step, the compression in this state and maintaining the diameter of the stent 2 at the first diameter for a certain period of time. As a result, the amount of the balloon 1 pinched by the stent 2 increases or the like, so that the stent 2 is more firmly fixed to the balloon 1 and the retention is stabilized. In the first maintenance step, a load of 5 N or more and 10 N or less (5 N to 10 N) per length of 1 mm in the axial direction of the stent 2 may be applied to the stent 2 inward in the radial direction.

In the second diameter reduction step, the opening diameter of the crimping head 9 may be reduced to the second diameter. That is, in the second diameter reduction step, the stent 2 may be compressed until the diameter of the stent 2 becomes the second diameter. As a result, the diameter reduction of the stent 2 can be performed until the diameter of the stent 2 reaches the second diameter.

The second maintenance step is a step of stopping, after the diameter of the stent 2 reaches the second diameter in the second compression step, the compression in this state and maintaining the diameter of the stent 2 at the second diameter for a certain period of time. As a result, the cross-sectional shapes of the balloon 1 and the stent 1 are made uniform, and the retention is stabilized. In the second maintenance step, a load of 5 N or more and 10 N or less (5 N to 10 N) may be applied to the stent 2 inward in the radial direction per length of 1 mm in the axial direction of the stent 2.

Incidentally, the second diameter may be equal to or smaller than the first diameter. That is, the second diameter may be the same as the first diameter. The second diameter may be smaller than the first diameter. The second diameter may be, for example, 3.0 mm or smaller. Hereinafter, a target value of the diameter reduction in each of the diameter reduction steps, such as the first diameter and the second diameter, is sometimes referred to as a final diameter.

The final diameter may be equal to or smaller than the diameter D of the proximal-side joint portion 16. The final diameter (particularly the second diameter) is preferably smaller than the diameter D of the proximal-side joint portion 16 (less than the diameter D). As a result, the diameter can be decreased. For example, there is a case where it is possible to provide the stent delivery system 200 in which the diameter of the stent 2 is equal to or smaller than the diameter D of the proximal-side joint portion 16 and equal to or larger than the diameter of the inner tube 7. Note that it is preferable that the stent 2 and the outer tube 6 do not overlap in the radial direction when the final diameter is equal to or smaller than the diameter D of the proximal-side joint portion 16.

Among the final diameters, the first diameter may be larger than the diameter D (more than the diameter D), and the second diameter may be smaller than the diameter D (less than the diameter D). As a result, manufacturing time of the stent delivery system 200 can be shortened by shortening step time of the first compression step and the first release step in the first diameter reduction step.

As described above, the second diameter reduction step may be repeated twice (two times) or more. In this case, the second diameter in a certain second diameter reduction step may be made smaller than the second diameter in the immediately previous second diameter reduction step. That is, the final diameter may be sequentially reduced as the second diameter reduction step is repeated.

The first release step and the second release step are steps of releasing the compression after compressing the stent 2 to the final diameter. Here, releasing the compression means ending the pressing to relax the stent 2 and the balloon 1, and is specifically performed by making the opening diameter of the crimping head 9 larger than the final diameter. When the opening diameter of the crimping head 9 is enlarged, the diameters of the stent 2 and the balloon 1 are enlarged (recoil).

After the first diameter reduction step (after the first release step), the diameters (diameters after the recoil) of the stent 2 and the balloon 1 are smaller than those at the start of the first diameter reduction step. Therefore, when the compression is released in the first diameter reduction step, that is, in the first release step, a diameter (hereinafter, referred to as a first release diameter) of the hole portion 90 at the end of the first release step may be equal to or smaller than the diameter (the opening diameter of the crimping head 9 at the start of the first compression step of the first release step, hereinafter referred to as a first start diameter) of the hole portion 90 at the start of the first diameter reduction step. Note that the first start diameter in the first diameter reduction step performed for the first time (first) is the opening diameter of the crimping head 9 at the time when an inner surface of the hole portion 90 comes into contact with the entire outer peripheral surface of the stent 2, in other words, at the time when the compression of the stent 2 is started.

The first start diameters at the second and subsequent times are preferably made larger than the diameter D of the proximal-side joint portion 16. As a result, disturbance in the manner of folding the balloon 2 is suppressed, and the retention is improved.

As described above, after the first diameter reduction step, the diameters of the stent 2 and the balloon 1 (diameters after the recoil) are smaller than those at the start of the first diameter reduction step, and thus, the opening diameter of the crimping head 9 at the start of the second diameter reduction step (the diameter of the hole portion 90, hereinafter referred to as a second start diameter) is smaller than the first start diameter. In the present embodiment, the second start diameter of the first second diameter reduction step is the same as the first release diameter of the immediately previous first release step.

After the second diameter reduction step (after the second release step), the diameters (diameters after the recoil) of the stent 2 and the balloon 1 are smaller than the second start diameter of the second diameter reduction step. Therefore, when the compression is released in the second diameter reduction step, that is, in the second release step, a diameter (hereinafter, referred to as a second release diameter) of the hole portion 90 at the end of the second release step may be smaller than the diameter (hereinafter, referred to as the second start diameter) of the hole portion 90 at the start of the second diameter reduction step.

In the second release step of the second diameter reduction step performed last, the opening diameter of the crimping head 9 may be enlarged to be equal to or larger than the first start diameter in order to easily take out (remove) the stent 2 and the balloon 1 from the crimping head 9.

As described above, the second diameter reduction step is preferably repeated twice (two times) or more, but the repetition of the second diameter reduction step may be ended in the following cases.

As an example, the repetition of the second diameter reduction step is preferably ended when the diameter of the stent 2 after the recoil occurring after the second diameter reduction step is equal to or smaller than a predetermined value (as an example, 1.02 mm). That is, the repetition of the second diameter reduction step may be ended if the diameter of the stent 2 is decreased to the predetermined value as a target value. As a result, the diameter can be efficiently decreased.

In addition, the repetition of the second diameter reduction step is preferably ended when a change rate (decrease rate) of the diameter of the stent 2 in a case where a load of 5 N or more and 10 N or less (5 N to 10 N) per length of 1 mm in the axial direction of the stent 2 is applied inward in the radial direction of the stent 2 becomes a predetermined amount x (%) or less. As a result, the diameter can be efficiently decreased.

Here, the change rate of the diameter of the stent 2 is a value obtained by dividing an absolute value of a difference $\Delta d$, obtained by subtracting a diameter d2 of the stent 2 after the application of the above load from a diameter d1 of the stent 2 before the application of the above load, by the diameter d1 and multiplying the division result by 100.

In a case where the second compression step in the second diameter reduction step is performed by applying a load of 5 N or more and 10 N or less (5 N to 10 N) per length of 1 mm in the axial direction of the stent 2 inward in the radial direction to the stent 2, the diameter d1 is a diameter of the stent 2 immediately before the start of the second diameter reduction step, and the diameter d2 is a diameter of the stent 2 after recoil occurring after the second diameter reduction step.

The predetermined amount x is, for example, 1.54% or less, preferably 1.44% or less, more preferably 0.66% or less, and still more preferably 0.60% or less. The predetermined amount x is allowed to be 0.08% or more.

In a case where the diameter reduction of the stent 2 in the second diameter reduction step is performed with a load of 5 N or more and 10 N or less (5 N to 10 N) per length of 1 mm in the axial direction of the stent 2, an amount of the decrease in the diameter of the stent 2 in this step corresponds to the difference $\Delta d$, and the diameter d2 is a diameter of the stent 2 immediately after the step.

In the crimping method according to the present embodiment, the pressurization step of supplying fluid to the balloon 1 to inflate the balloon 1 and pressing the outer peripheral surface of the balloon 1 against the inner side of the stent 2 is performed in the process of crimping the stent 2 to the balloon 1 as described above. Through the pressurization step, the amount of the balloon 1 pinched by the stents 2 increases, and the retention is improved and stabilized. In addition, adhesion between the surface of the stent 2 on the inner side in the radial direction and the outer surface of the balloon 1 is stabilized, and the retention is improved.

The pressurization step may be performed in a state where the stent 2 is recoiled by the first release step. When the pressurization step is performed in the state where the stent 2 is recoiled, the manner of folding the balloon 2 is made uniform, and the retention is more favorably stabilized.

The pressurization step is preferably performed in a state where the diameter of the stent 2 is made larger than the recoil diameter (the maximum diameter to which the stent 2 is naturally expanded in diameter) in the state where the stent 2 is recoiled in the first release step, which may make the manner of folding the balloon 2 uniform and stabilize the retention. In the pressurization step, the diameter of the stent 2 is preferably made larger than the recoil diameter and equal to or smaller than the first start diameter.

Note that a period during which the stent 2 is in the recoiled state by the first release step is a period during the first release step, a period immediately after the first release step and immediately before the first compression step in the next first diameter reduction step, a period during the first compression step in the first diameter reduction step performed immediately after the first release step, a period immediately after the first release step and immediately before the second compression step in the second diameter reduction step, and during the second compression step in the second diameter reduction step performed immediately after the first release step. That is, the pressurization step may be performed during these steps.

As described above, the pressurization step may be performed during the first release step. As a result, since the balloon 1 can be pinched by the stent 2 after the balloon 1 is once folded through the first compression step (after the balloon 1 has a folding shape), the manner of folding the balloon 2 is made uniform, and the retention is stabilized.

As described above, the pressurization step may be performed during a period from the first release step to the second compression step immediately after the first release step or the second compression step. In addition, the pressurization step may be performed over a period from before the first release step to after the first compression step immediately after the first release step or after the second compression step. As a result, time for the pressurization step is extended without extending the entire step time, and the retention is more favorably stabilized.

As described above, the pressurization step may be performed during a period immediately after the first release step and immediately before the second compression step in the next first diameter reduction step or during a period immediately after the first release step and immediately before the second compression step in the second diameter reduction step. Even in this case, since the balloon 1 can be pinched by the stent 2 after the balloon 1 is once folded through the first compression step (after the balloon 1 has a folding shape), the retention is improved. In addition, the variation in the retention is reduced.

The pressurization step may include a holding step of keeping the pressure of the fluid supplied to the balloon 1 and the diameter of the stent 2 constant for a predetermined period of time (between, for example, 10 seconds and 45 seconds, 30 seconds as an example), which makes the manner of folding the balloon 2 uniform and stabilizes the retention. The holding step may be performed during a period immediately after the first release step and immediately before the first compression step in the next first diameter reduction step or during a period immediately after the first release step and immediately before the second compression step of the second diameter reduction step.

In this holding step, the diameter of the stent 2 is preferably made larger than the recoil diameter, which may make the manner of folding the balloon 2 uniform and further stabilize the retention.

Note that, in the present embodiment, it is not excluded to perform the pressurization step during a period other than the periods or the middle of the steps exemplified above. For example, the pressurization step may be performed before the first diameter reduction step, during the first diameter reduction step, during the first maintenance step, and during the second maintenance step.

When the pressurization step is performed, the second diameter reduction step is preferably repeated twice (two times) or more, which may stabilize the retention. When the first pressurization step or the second post-pressurization step is performed, it is preferable to further perform the second diameter reduction step in which no pressurization step is performed after the pressurization step. It is preferable that the second diameter reduction step including no pressurization step performed after the pressurization step is repeated, for example, two times or more, and preferably three to five times, which may further stabilize the retention.

Figure 7:
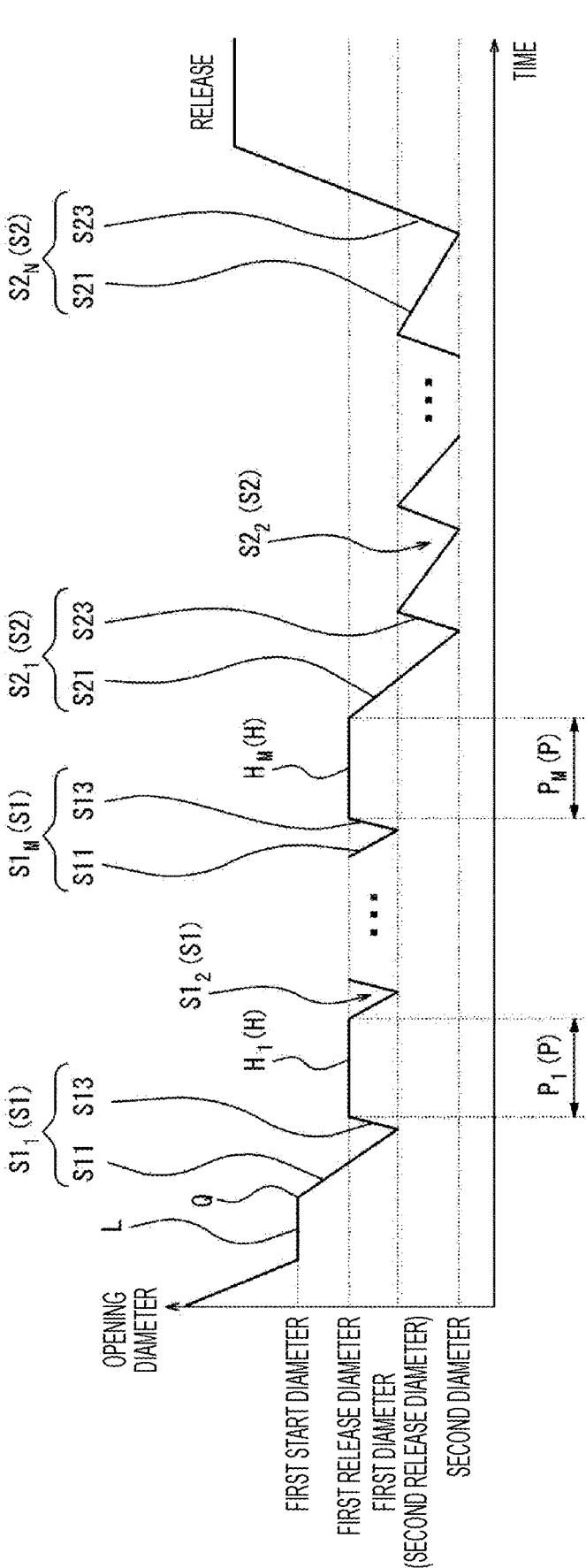
FIG. 7 is a graph illustrating an example of a method for manufacturing the stent delivery system in the relationship between an opening diameter of the crimping head and step elapsed time.

FIG. 7 illustrates a graph illustrating an example of the method (crimping method) for manufacturing the stent delivery system described above in the relationship between the opening diameter of the crimping head 9 (see FIGS. 5 and 6 above) of the crimping device and step elapsed time. In the graph of FIG. 7, the vertical axis represents the opening diameter of the crimping head 9 (opening diameter in FIG. 7), and the horizontal axis represents the step elapsed time in the method for manufacturing the stent delivery system. In the graph of FIG. 7, a solid line L indicates the opening diameter of the crimping head 9.

In FIG. 7, reference sign S1 denotes the first diameter reduction step. The example illustrated in FIG. 7 illustrates a case where the first diameter reduction step is performed M times (where M is a natural number). Reference sign $S1_j$ such as reference sign $S1_1$ denotes the j-th (where j is a natural number equal to or less than M) first diameter reduction step. Reference sign S11 denotes the first compression step. Reference sign S13 denotes the first release step.

Reference sign Q denotes the start of the first diameter reduction step. In the example illustrated in FIG. 7, the first start diameter in the second and subsequent first diameter reduction steps are the same as the first release diameter in the immediately previous release step. The first start diameter in the first diameter reduction step is larger than the diameter D of the proximal-side joint portion 16. The first release diameter is larger than the recoil diameter.

Reference sign H denotes the holding step. Reference sign $H_j$ such as reference sign $H_1$ denotes the j-th holding step. The holding step is performed immediately after the first release step. In addition, the holding step is performed before the first compression step of the first release step or the second compression step. Reference sign P denotes a period during which the pressurization step is performed. Reference sign $P_j$ such as reference sign $P_1$ denotes the j-th pressurization step. In the example illustrated in FIG. 7, the period during which the pressurization step is performed is the same as a period during which the holding step is performed.

The example illustrated in FIG. 7 illustrates a case where the first diameter reduction step in which the final diameter is the first diameter is performed M times, and then the second diameter reduction step in which the final diameter is the second diameter is performed N times (where N is a natural number). In the example illustrated in FIG. 7, the first diameter is larger than the diameter D (see FIG. 3) of the proximal-side joint portion 16, and the second diameter is smaller than the diameter D.

In FIG. 7, reference sign S2 denotes the second diameter reduction step. Reference sign $S2_i$ such as reference sign S21 denotes the i-th (where i is a natural number less than or equal to N) second diameter reduction step. Reference sign S21 denotes the second compression step. Reference sign S23 denotes the second release step.

The second start diameter in the second diameter reduction step performed first (for the first time) is the same as the first release diameter in the first diameter reduction step. In the example illustrated in FIG. 7, the second release diameter in the second release step excluding the last one is the same as the first diameter. That is, the second release diameter is larger than the diameter D (see FIG. 3) of the proximal-side joint portion 16.

The second release diameter in the last second diameter reduction step is set to be equal to or larger than the first start diameter, for example, and crimping is terminated.

Figure 8:
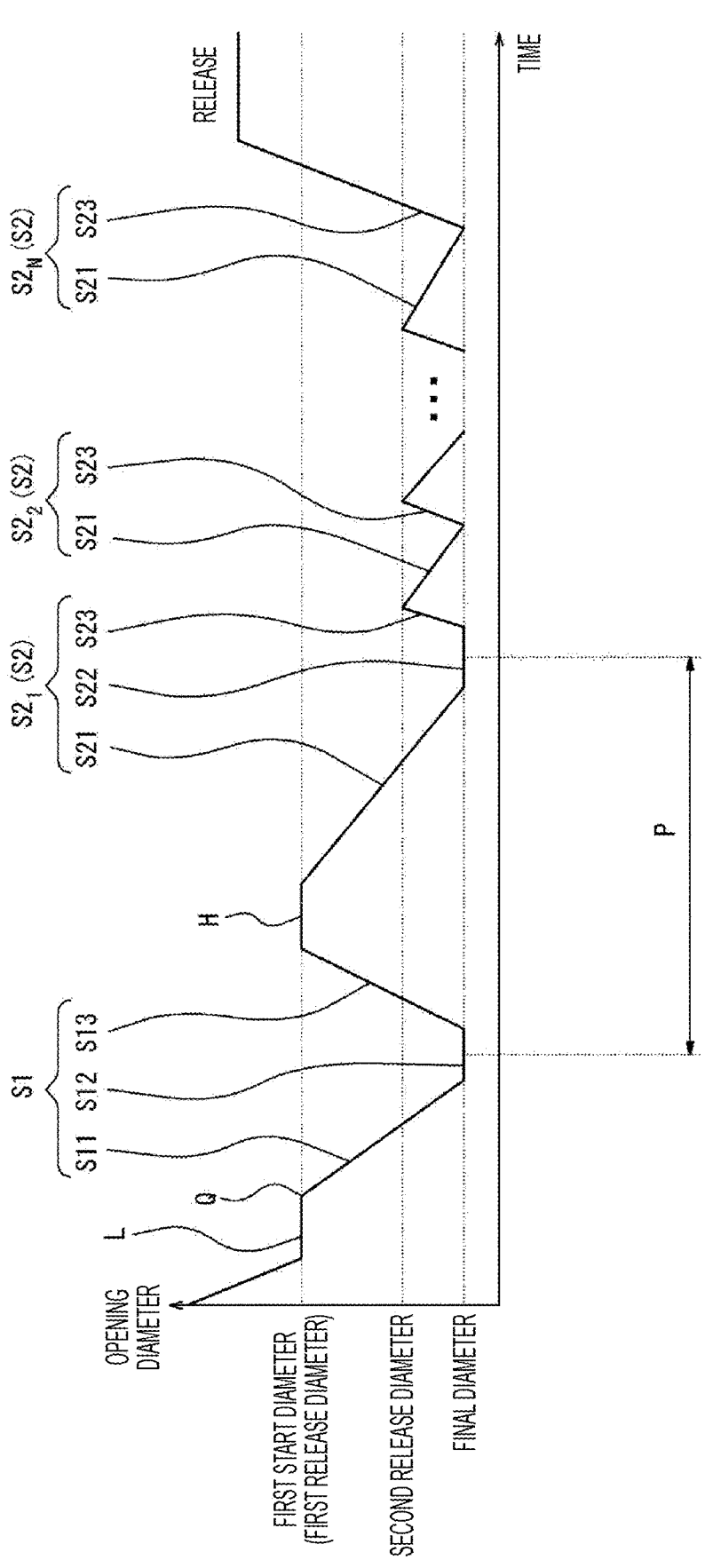
FIG. 8 is a graph illustrating another example of the method for manufacturing the stent delivery system in the relationship between the opening diameter of the crimping head and the step elapsed time.

FIG. 8 illustrates a graph illustrating another example of the method (crimping method) for manufacturing the stent delivery system described above in the relationship between the opening diameter of the crimping head 9 (see FIGS. 5 and 6 above) of the crimping device and the step elapsed time. Similarly to FIG. 7, in the graph of FIG. 8, the vertical axis represents the opening diameter of the crimping head 9 (opening diameter in FIG. 8), and the horizontal axis represents the step elapsed time in the method for manufacturing the stent delivery system. In the graph of FIG. 8, a solid line L indicates the opening diameter of the crimping head 9.

In FIG. 8, reference sign S1 denotes the first diameter reduction step. Reference sign S11 denotes the first compression step. Reference sign S12 denotes the first maintenance step. Reference sign S13 denotes the first release step. Reference sign Q denotes the start of the first diameter reduction step. In the example illustrated in FIG. 8, the first release diameter in the first release step is the same as the first start diameter in the first diameter reduction step (S1). The first release diameter is larger than the recoil diameter.

The example illustrated in FIG. 8 illustrates a case where the final diameter (first diameter) in the first diameter reduction step and the final diameter (second diameter) in the second diameter reduction step are the same. These final diameters are smaller than the diameter D (see FIG. 3) of the proximal-side joint portion 16.

In FIG. 8, reference sign S2 denotes the second diameter reduction step. The example illustrated in FIG. 8 illustrates a case where the second diameter reduction step is performed N times (where N is a natural number). Reference sign $S2_i$ such as reference sign $S2_1$ denotes the i-th (where i is a natural number less than or equal to N) second diameter reduction step. In this example, the second diameter reduction step is performed N times after the first diameter reduction step. Reference sign S21 denotes the second compression step. Reference sign S22 denotes the second maintenance step. Reference sign S23 denotes the second release step. Reference sign S23 denotes the second release step. FIG. 8 illustrates a case where the second maintenance step is performed only in the second diameter reduction step performed first.

In FIG. 8, the second release diameter in the second release step of the second diameter reduction step is smaller than the first release diameter and larger than the diameter D (see FIG. 3) of the proximal-side joint portion 16.

Reference sign H denotes the holding step. The holding step is performed during a period between the first release step in the first diameter reduction step and the second compression step in the immediately subsequent (first) second diameter reduction step.

Reference sign P denotes a period during which the pressurization step is performed. In the example illustrated in FIG. 8, the period in which the pressurization step is performed is from before the start and after the end of the holding step. More specifically, the case where the pressurization step is performed during a period from the first maintenance step in the first diameter reduction step, that is, before the first release step, to the second maintenance step in the immediately subsequent (first) second diameter reduction step is illustrated.

EXAMPLES

Hereinafter, a stent delivery system and a method for manufacturing the same will be described based on Examples.

Example 1

In this Example, in a state where a balloon disposed on a shaft having an inner tube and an outer tube was inserted into a tube of a stent having a diameter (outer diameter) of 2.0 mm, the stent and the balloon were inserted into a crimping head of a crimping device and crimped to crimp the stent on the balloon by a crimping method to be described below. Then, retention of the crimped stent and a variation of the crimped stent were measured. As the balloon and the stent, "Ultimaster Nagomi®" manufactured by Terumo Corporation was used.

The balloon used in this Example is fused and joined to an outer peripheral surface of the outer tube on the proximal side, and a diameter (outer diameter) of such a proximal-side joint portion is 1.0 mm. The balloon is fused and joined to an outer peripheral surface of the inner tube on the distal side, and a diameter (outer diameter) of such a distal-side joint portion is 0.6 mm. The balloon was folded in advance to have three wings prior to insertion into the stent. The balloon is made of a polyamide resin. Note that the inner tube has an outer diameter of 0.25 mm, and the outer tube has an outer diameter of 0.65 mm.

The stent used in this Example is a wire mesh stent made of L-605 alloy.

In Example 1, the stent was crimped on the balloon by the crimping method according to the example illustrated in FIG. 8 described above.

Note that, prior to the start of a first diameter reduction step, first, the stent was temporarily fixed to the balloon. This temporary fixing was performed by inserting the stent and the balloon into the crimping head of the crimping device and lightly crimping the stent and the balloon in a state where the balloon disposed on the shaft was inserted into the tube of the stent.

The first diameter reduction step was performed once.

A first start diameter in the first diameter reduction step is 2.0 mm which is the same as the diameter of the stent.

A final diameter (first diameter) in the first diameter reduction step was set to 1.8 mm, which is smaller than the diameter of the proximal-side joint portion, to be smaller than the diameter of the proximal-side joint portion.

The first compression step was performed until reaching the final diameter while maintaining a state where a load of 5 N or more and 10 N or less (5 N to 10 N) per length of 1 mm in the axial direction of the stent was applied inward in the radial direction of the stent by sequentially reducing a hole diameter of the crimping head. In this Example, a first maintenance step was omitted. After the first compression step, a first release step was performed. The first release diameter was 1.3 mm smaller than the first start diameter and larger than a recoil diameter.

As described later, a holding step was performed after the first release step. After the holding step, a second diameter reduction step was repeated.

A pressurization step was performed during a period from the first maintenance step in the first diameter reduction step, that is, before the first release step, to a second maintenance step in the immediately subsequent (first) second diameter reduction step. In the pressurization step, the inside of the balloon was pressurized and maintained at 1.4 MPa, and the pressure in the balloon was released at the end of the pressurization step.

The holding step was performed during a period between the first release step in the first diameter reduction step and a second compression step in the immediately subsequent (first) second diameter reduction step. In the holding step, the diameter of the stent was kept at the first release diameter (1.3 mm). As a result, in the holding step, the diameter of the stent was made larger than the recoil diameter by pressurization of the balloon.

After the holding step, the second diameter reduction step was repeated 15 times. Second release diameters in the first to fourteenth second diameter reduction steps were set to 1.2 mm to be smaller than the first release diameter. That is, the second release diameters in the second to fifteenth second diameter reduction steps were set to 1.2 mm. The second release diameter in the fifteenth second diameter reduction step was made larger than the first start diameter. In this Example, the second maintenance step was performed only in the first diameter reduction step performed first, and the second maintenance step was omitted in the second and subsequent second diameter reduction steps.

The final diameter (second diameter) in each of the second diameter reduction steps was set to 0.75 mm to be smaller than the diameter of the proximal-side joint portion.

Similarly to the first compression step, a second compression step in the second diameter reduction step was performed until reaching the final diameter while maintaining a state where a load of 5 N or more and 10 N or less (5 N to 10 N) per length of 1 mm in the axial direction of the stent was applied inward in the radial direction of the stent by sequentially reducing a hole diameter of the crimping head.

Two stents crimped on the balloons as described above were manufactured, and an average value of the retention (holding forces) of these stents was acquired. As a result, the average value of the retention was 1.76 (N). In addition, a variation (standard deviation σ) of the retention was 0.027 (N).

Note that the retention is the force of holding the stent in a state of being crimped on the balloon. The retention in this Example is a value measured in accordance with ASTM F2394-07 (initial peak displacement force described in Reapproved 2022), and is a pulling force when the stent falls off the balloon when the stent is pulled in the axial direction with respect to the balloon.

Comparative Example 1

In Comparative Example 1, the stent was crimped on the balloon in the same manner as in Example 1 except that the first release diameter in the first release step performed in Example 1 was set to 1.2 mm to be the same as the second release diameter, a pressurization step of pressurizing and keeping the inside of the balloon at 1.4 MPa was performed during a period from before the start of the first diameter reduction step to the middle of the first maintenance step, and the holding step and all the second maintenance steps were omitted. Then, the retention of the crimped stent was measured.

Two stents crimped on the balloons as described above were manufactured, and an average value of the retention (holding forces) of these stents and a variation thereof were acquired. As a result, the average value of the retention was 2.32 (N). In addition, the variation (standard deviation σ) of the retention was 0.175 (N).

From results of Example 1 and Comparative Example 1 described above, it was found that the variation in the retention was reduced by performing the pressurization step during or after the first release step. The reason for such a result is considered that the manner of folding the balloon 2 is uniform since the balloon can be pinched by the stent after the balloon is once folded through the first compression step (after the balloon has a fold-up shape).

In addition, it was found that the variation in the retention was reduced by performing the pressurization step by making the diameter of the stent larger than the recoil diameter. The reason for this is considered that the manner of folding the balloon was made uniform or disturbance in the manner of folding was suppressed so that an amount of the balloon pinched by the stent increased so that a holding state of the stent by the balloon was stabilized. In addition, the reason is considered that adhesion between a surface of the stent on the inner side in the radial direction and an outer surface of the balloon was improved by the pressurization step so that the holding state of the stent by the balloon was stabilized.

As described above, it is possible to provide the stent delivery system and the method for manufacturing the same that achieve a decrease in diameter of a balloon catheter on which the stent is crimped.

Note that the embodiments disclosed in the present specification are examples, and the embodiments of the present disclosure are not limited thereto, and can be appropriately modified within a scope not departing from the object of the present disclosure.

The detailed description above describes a method for manufacturing a stent delivery system. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A method for manufacturing a stent delivery system, the method comprising:

a first diameter reduction step including a first compression step of compressing a stent inward in a radial direction of the stent in a state where a balloon is inserted into a tube of the stent formed in a tubular shape to reduce diameters of the stent and the balloon, and a first release step of releasing the compression after the first compression step;

a pressurization step of supplying fluid to the balloon to inflate the balloon and pressing the balloon against an inner side of the stent, wherein the pressurization step is performed during or after the first release step; and a second diameter reduction step performed after the first diameter reduction step, the second diameter reduction step including a second compression step of compressing the stent inward in the radial direction of the stent to reduce the diameters of the stent and the balloon, and a second release step of releasing the compression after the second compression step, wherein the pressurization step is performed during the second compression step.

2. The method for manufacturing the stent delivery system according to claim 1, wherein the pressurization step is performed during a period from the first release step to the second compression step.

3. The method for manufacturing the stent delivery system according to claim 2, wherein the pressurization step includes a holding step of keeping pressure of the fluid supplied to the balloon and the diameter of the stent constant for a predetermined period of time.

4. The method for manufacturing the stent delivery system according to claim 1, wherein the pressurization step is performed over a period from before the first release step to after the second compression step.

5. The method for manufacturing the stent delivery system according to claim 1, wherein the pressurization step is performed after the first release step and before the second compression step.

6. The method for manufacturing the stent delivery system according to claim 1, wherein the second diameter reduction step is repeated two or more times.

7. The method for manufacturing the stent delivery system according to claim 1, wherein the pressurization step in the first release step makes the diameter of the stent larger than a recoil diameter at which the stent is recoiled by the first release step.

8. A method for manufacturing a stent delivery system, the method comprising:

compressing a stent inward a first time in a radial direction of the stent in a state where a balloon is inserted into a tube of the stent formed in a tubular shape to reduce diameters of the stent and the balloon, and releasing the compression after the compressing of the stent inward the first time;

compressing the stent inward a second time in the radial direction of the stent to reduce the diameters of the stent and the balloon, and releasing of the compression of the stent after the compressing of the stent inward the second time; and supplying fluid to the balloon to inflate the balloon and press the balloon against an inner side of the stent.

9. The method for manufacturing the stent delivery system according to claim 8, further comprising:

performing the supplying of the fluid to inflate the balloon and press the balloon against the inner side of the stent during or after the compressing of the stent inward the first time.

10. The method for manufacturing the stent delivery system according to claim 8, further comprising:

performing the supplying of the fluid to inflate the balloon and press the balloon against the inner side of the stent during the compressing of the stent inward the second time.

11. The method for manufacturing the stent delivery system according to claim 10, further comprising:

performing the supplying of the fluid to inflate the balloon and press the balloon against the inner side of the stent during a period from the releasing of the compression after the compressing of the stent inward the first time to the compressing the stent inward a second time.

12. The method for manufacturing the stent delivery system according to claim 11, further comprising:

keeping pressure of the fluid supplied to the balloon and the diameter of the stent constant for a predetermined period of time.

13. The method for manufacturing the stent delivery system according to claim 10, further comprising:

performing the supplying of the fluid to inflate the balloon and press the balloon against the inner side of the stent during the compressing of the stent inward over a period from before the releasing of the compression after the compressing of the stent inward the first time to after the releasing of the compression after the compressing of the stent inward the second time.

14. The method for manufacturing the stent delivery system according to claim 10, further comprising:

performing the supplying of the fluid to inflate the balloon and press the balloon against the inner side of the stent during the compressing of the stent inward after the releasing of the compression after the compressing of the stent inward the first time and before the releasing of the compression after the compressing of the stent inward the second time.

15. The method for manufacturing the stent delivery system according to claim 10, further comprising:

performing at least twice, the compressing of the stent inward the second time in the radial direction of the stent to reduce the diameters of the stent and the balloon, and the releasing of the compression of the stent after the compressing of the stent inward the second time.

16. The method for manufacturing the stent delivery system according to claim 8, further comprising:

increasing the diameter of the stent larger than a recoil diameter at which the stent is recoiled during the supplying of fluid to the balloon to inflate the balloon and pressing the balloon against the inner side of the stent during or after the compressing of the stent inward the first time.

17. A method for manufacturing a stent delivery system, the method comprising:

compressing a stent inward at a load of 5 N to 10 N per length of 1 mm in an axial direction of the stent inward in a radial direction of the stent in a state where a balloon is inserted into a tube of the stent formed in a tubular shape to reduce diameters of the stent and the balloon;

releasing the compression after the compressing of the stent; and supplying fluid to the balloon to inflate the balloon and press the balloon against an inner side of the stent.

18. The method for manufacturing the stent delivery system according to claim 17, further comprising:

performing the supplying of the fluid to inflate the balloon and press the balloon against the inner side of the stent during or after the compressing of the stent inward.

* * * * *